United States Patent [19]

Carmello et al.

[11] Patent Number: 5,262,574

[45] Date of Patent: * Nov. 16, 1993

[54] PROCESS FOR PREPARING 1,1,1-TRIFLUORO-2,2-DICHLOROETHANE BY HYDROFLUORINATION IN THE PRESENCE OF CATALYSTS

[75] Inventors: Diego Carmello, Mestre; Giorgio Guglielmo, Mirano, both of Italy

[73] Assignee: Ausimont S.p.A., Italy

[*] Notice: The portion of the term of this patent subsequent to Oct. 30, 2007 has been disclaimed.

[21] Appl. No.: 793,879

[22] Filed: Nov. 18, 1991

Related U.S. Application Data

[63] Continuation of Ser. No. 584,960, Sep. 19, 1990, Pat. No. 5,091,601, which is a continuation of Ser. No. 403,070, Sep. 5, 1989, Pat. No. 4,967,023, which is a continuation of Ser. No. 163,659, Mar. 3, 1988, abandoned.

Foreign Application Priority Data

Mar. 9, 1987 [IT] Italy .............................. 19622 A/87

[51] Int. Cl.$^5$ .................. C07C 17/20; C07C 19/02
[52] U.S. Cl. ....................... 570/166; 570/168; 570/169
[58] Field of Search ......................... 570/166, 169

[56] References Cited

U.S. PATENT DOCUMENTS

| | | | |
|---|---|---|---|
| 3,178,484 | 4/1965 | Christoph, Jr. ............... | 570/166 |
| 3,258,500 | 6/1966 | Swamer et al. ............... | 570/169 |
| 3,650,987 | 3/1972 | Vecchio et al. ............... | 570/166 |
| 3,755,477 | 8/1973 | Firth et al. .................. | 260/653.4 |
| 3,787,331 | 1/1974 | Groppelli et al. ............. | 252/442 |
| 3,793,229 | 2/1974 | Groppelli et al. ............. | 570/166 |
| 4,088,704 | 5/1978 | Nychka et al. ................ | 260/653 |
| 4,147,733 | 4/1979 | Fiske et al. ................. | 260/653 X |
| 4,843,181 | 6/1989 | Gumprecht et al. ............ | 570/169 |
| 4,967,023 | 10/1990 | Carmello et al. ............. | 570/166 |

*Primary Examiner*—Joseph E. Evans
*Attorney, Agent, or Firm*—Morgan & Finnegan

[57] ABSTRACT

A process for preparing 1,1,1-trifluoro-2,2-dichloroethane by hydrofluorination, in the gas phase, of perchloroethylene in the presence of a catalyst comprising chrome oxides supported on AlF$_3$ in the gamma and/or beta form.

3 Claims, No Drawings

PROCESS FOR PREPARING 1,1,1-TRIFLUORO-2,2-DICHLOROETHANE BY HYDROFLUORINATION IN THE PRESENCE OF CATALYSTS

This is a continuation of co-pending application Ser. No. 07/584,960 filed Sep. 19, 1990, now U.S. Pat. No. 5,091,601, which is a continuation of U.S. Ser. No. 07/403,070, filed Sep. 5, 1989, now U.S. Pat. No. 4,967,023; which is a continuation of U.S. Ser. No. 07/163,659, filed Mar. 3, 1988, now abandoned.

This invention relates to a process for preparing 1,1,1-trifluoro-2,2-dichloroethane by hydrofluorination, in the gas phase, of perchloroethylene in the presence of a catalyst comprising $Cr_2O_3$ supported on $AlF_3$.

BACKGROUND OF THE INVENTION

Well known is the requirement of having available industrial processes for preparing 1,1,1-trifluoro-2,2-dichloroethane with good yields.

It is well known how to prepare 1,1,1-trifluoro-2,2-dichloroethane starting from perchloroethylene in the presence of catalysts based on $Cr_2O_3$. See for example Italian patent application No. 24689 A/78 and U.S. Pat. No. 3,755,477.

The process described in U.S. Pat. No. 3,755,477 leads to yields of the mentioned product equal to about 20% and it cannot be utilized on a commercial scale because of the too high amount of by-products.

An alternative process (U.S. Pat. No. 4,145,368 and U.S. Pat. No. 4,192,322) for preparing the compound of the invention comprises reacting 1,1,1-trifluoro-2-chloroethane with chlorine. The yields of the compound of the invention are very low. However to increase the useful product yields, it is possible, according to the above-cited patents, to react the obtained reaction mixture with further starting product 1,1,1-trifluoro-2-chloroethane in the presence of catalysts such as $Cr_2O_3$, oxyfluorides or activated carbon.

Also when using this method, the yields of useful product 1,1,1-trifluoro-2,2-dichloroethane are of the order of 14%.

This process is not utilizable on an industrial scale as it requires two reaction steps plus a third step, which is necessary to prepare the starting product. Furthermore, the contact time of the reagents used in the step where the catalyst based on $Cr_2O_3$ or the ones cited above is of the order of 90 seconds. These times are too long for an industrial process in the gas phase, because it requires too large reactors.

Processes for the liquid-phase-hydrofluorination of halogenated olefins for preparing chlorofluorohydrocarbons are well known in the art, such processes using, as catalysts, for example $TaF_5$, $BF_3$, $SbCl_3F_2$.

When perchloroethylene is utilized as a starting product, it is not possible to obtain the product of the invention.

This product is obtainable with very low yields, of about 10%, by previously reacting perchloroethylene with HF and by subsequent hydrofluorination in the presence of $TaF_5$. See, for example, Journal Fluorine Chemistry, 13 (1979), 7–18, "Chemistry of Hydrogen Fluoride v. Catalysts for Reaction of HF with Halogenated Olefins", A. E. Feiring.

In the art there are known many modifications of the various types of fluorination catalysts which are utilized for preparing perhalo-compounds of chlorofluorohydrocarbons.

There are known, in fact, fluorination catalysts based on chrome oxides, oxyfluorides, fluorides, or copper, iron, nickel, manganese, cobalt fluorides, etc. carried on $Al_2O_3$, $AlF_3$, activated carbon, $CaF_2$.

However it is well known that carriers different from the fluorinated ones, in the presence of HF tend to give the corresponding fluorinated carriers. Therefore in practice, the reaction which leads to fluorocarbons is carried out in the presence of a fluorinated carrier.

However, the product of the invention is not exemplified in any patent, except the ones mentioned above.

U.S. Pat. No. 3,258,500 describes various fluorination catalysts, among which is $Cr_2O_3$. The 1,1,1-trifluoro-2,2-dichloroethane yields are of about 16% if it is operated at about 300° C. and they sink to about 3.5% if it is operated at 400° C. In said patent, column 7, lines 30–52, it is specified that it is essential, when using these catalysts, to operate at exactly defined temperatures to obtain good conversions to the desired useful product. As mentioned above, the best mode of this patent for the product 1,1,1-trifluoro-2,2-dichloroethane indicates 16% as the best result.

Furthermore, this patent indicates, as a possible alternative, the possibility of supporting chrome oxide on various inert supports; for example $Al_2O_3$ (column 6, lines 23–54). Nevertheless the results so obtained are of little interest as the yields decrease.

The process according to said patent is in any case of low industrial value because the by-product amount is too high.

DETAILED DESCRIPTION OF THE INVENTION

It has surprisingly been found that it is possible to prepare 1,1,1-trifluoro-2,2-dicloroethane by a process which is readily practicable on an industrial scale, if perchloroethylene is used as a starting product.

Thus, the object of the present invention is a process for preparing 1,1,1-trifluoro-2,2-dichloroethane, which comprises reacting perchloroethylene with HF in the gas phase in the presence of catalysts which comprise $Cr_2O_3$ supported on $AlF_3$, in the gamma and/or beta form.

Generally, the amount of $Cr_2O_3$ ranges from 1 to 15% by weight, calculated as Cr on the catalyst. The percentage of $Cr_2O_3$ is a function of the surface area of $AlF_3$ in the gamma form.

Carriers having a high surface area, of the order of 25–30 $m^2/g$, are generally preferred. In this case it is possible to use $Cr_2O_3$ amounts also lower than 5%.

If the surface area is lower, higher $Cr_2O_3$ amounts are generally utilized.

The carrier can be in the form of powders having particle size generally ranging from 20 to 200 micron. If necessary, it can be also in the form of pellets.

$AlF_3$ may contain, besides the gamma and/or beta form, also the delta form, generally also in percentages up to 30% by weight.

$AlF_3$ in the alpha form can be present too, although it should be preferably limited because it was observed that this form is little active.

The catalyst of the invention can be prepared in various manners, one of the preferred methods being the following: the $AlF_3$ carrier in the crystallographic forms is wet or dry impregnated, according to a technique known in the art, with a solution of a soluble trivalent chromium salt, for example $CrCl_3.6H_2O$.

The catalyst is then dried to remove the water contained therein. Then it is charged into a reactor and subjected to an activation treatment with air or nitrogen either or not in the presence of steam.

The activation treatment is generally carried out at temperatures from 200° to 600° C., preferably from 350° C. to 500° C., to convert chrome to the oxide form.

The above-mentioned allotropic structures of $AlF_3$ are known and are characterized by the X-ray diffraction pattern, as is reported in J.C.P.D.S. 1981 and in French patent No. 1,383,927 to Du Pont.

The above-considered gamma$_c$, delta$_c$ and beta$_c$ phases are the ones described in French patent No. 1,383,927 by J. Christoph and J. Teufer. The alpha phase is described in Anal. Chem. 29, 984 (1957).

After a prolonged use, the catalyst activity can be restored by a treatment with air at high temperatures (from 350° to 500° C.), however, these regenerations are to be conducted cautiously as they can impair the catalyst life. It was observed, for example, that the heat treatments can promote the irreversible conversion of the aluminium trifluoride active phases to the alpha-$AlF_3$ inactive phase.

The molar ratio between reagents HF and $C_2Cl_4$ is at least of 3:1, in particular of 5:1. It was ascertained that lower molar ratios lead to low conversions of $C_2Cl_4$ and, in any case, shorten the catalyst life as they favour the deposition of carbon and organic pitches onto the catalyst surface, thereby reducing the catalytic activity.

The reaction temperature ranges from 250° to 500° C. and preferably from 300° to 400° C.

The contact time between reagents and catalyst mass ranges from 1 second to 30 seconds, preferably from 3 to 15 seconds.

The 1,1,1-trifluoro-2,2-dichloroethane yields obtained through the process of the invention are of the order of 15-20% by moles if it is operated under the above-mentioned conditions.

However, contrary to expectation, in the process of the invention the other reaction products consist, besides for the most part of the unreacted starting product, of partially fluorinated intermediates, while only about 20% by moles consists of highly fluorinated low-boiling products.

By simple stripping it is possible to separate the unreacted perchloroethylene and the partially fluorinated intermediates and to recycle them again to obtain the product of the invention. The feeding mixture in the recycle is added with fresh perchloroethylene.

In this manner, the yields of 1,1,1-trifluoro-2,2-dichloroethane product can reach 90% by moles.

This is a very important advantage of the process of the present invention with respect to the above-cited known processes for preparing 1,1,1-trifluoro-2,2-dichloroethane. As in the above-illustrated patents, the reaction by-products were so highly fluorinated that they could not be recycled.

For the purpose of a better comprehension of the present invention it is therefore useful to consider the net yield of 1,1,1-trifluoro-2,2-dichloroethane, intermediates and by-products.

As regards this invention, the term "net yield" means the following expression:

$$\frac{\text{moles of product obtained}}{\text{moles of converted raw material}} \times 100.$$

In the present invention, the net yield of by-products is very low, generally it is of 10%.

The utilization of the compound forming the object of the invention as well known in the art. In particular it is utilized as a fluid for aerosol or as a propellant.

EXAMPLES

The following examples are given merely to illustrate this invention, without being however a limitation thereof.

EXAMPLE 1

A) 240 g of aluminum trifluoride, consisting for 30% of delta-$AlF_3$, for 60% of gamma-$AlF_3$ and for the remaining 10% of beta-$AlF_3$ and alpha-$AlF_3$, were impregnated with a solution prepared by dissolving 52.3 g of $CrCl_3.6H_2O$ in 58 ml of distilled water. Aluminium trifluoride was composed of particles having diameters ranging from 20 to 200 micron, the average diameter being of 80 micron. Aluminium trifluoride was impregnated by dropping of the $Cr_2Cl_3.6H_2O$ under stirring. Subsequently the catalyst was partially dried in oven at 110° C. for 1.5 hours, whereafter it was placed into a tubular reactor made of Inconel 600, having an inside diameter of 5 cm, a height of 80 cm and being equipped on the bottom with a porous septum made of sinterized Inconel for uniformly distributing the gases entering from the bottom and for supporting the inactive catalytic bed. The thermocouples for the temperature measurements were placed in a sheath arranges in the middle of the reactor.

The catalyst placed in the abovesaid reactor was heated up to 200° C. in a nitrogen flow of 100 l/h. The $N_2$ flow was stopped and 100 l/h of air and 80 l/h of HF were sent to the reactor after having been reciprocally mixed in the preheater arranged upstream of the reactor. Heating was resumed in an air and HF stream until a temperature of 400° C. was reached. This temperature was maintained for 2 hours, whereafter the catalyst was cooled in a $N_2$ flow.

B) Using the catalyst so prepared and the same apparatus, 0.855 moles/h of $C_2Cl_4$ and 3.542 moles/h of HF were sent to the reactor. The reaction temperature was of 360° C. and the pressure was slightly higher than the atmospheric pressure. The contact time was of 5 seconds calculated as the ratio between non-fluidized catalyst volume and volumetric flow of the reagents fed at the reaction temperature and pressure. The gases outflowing from the reactor were drawn for 1 hour. After absorption of HCl and HF in water and after washing of the reaction product with an aqueous solution of NaOH, 141 g of product were recovered, the molar composition of which being as follows:

| | |
|---|---|
| $CF_3CHClF$ | 1.2% |
| $CF_3-CHCl_2$ | 5.1% |
| $CCl_2=CClF + CClF_2-CHCl_2$ | 5.0% |
| $C_2Cl_4$ | 88.0% |

The conversion of $C_2Cl_4$ was of 12%, while the net yield of $CF_3-CHCl_2$ was of 42.9% and the net yield of by-products was of 10%.

EXAMPLE 1A (COMPARATIVE TEST)

Into the apparatus of Example 1 there were charged 345 g of the aluminium trifluoride used for preparing the catalyst of Example 1. At a reaction temperature of 360° C. and at a pressure slightly higher than the atmospheric pressure, 0.886 moles/h of $C_2Cl_4$ and 3.44 moles/h of HF were fed. After a process analogous with the one described in Example 2, 147 g of a reaction product having the following molar composition were recovered:

| | |
|---|---|
| $CF_3$—$CHCl_2$ | traces |
| $CCl_2$=$CClF$ + $CClF_2$—$CHCl_2$ | 1.1% |
| $C_2Cl_4$ | 98.5% |

Therefore, aluminium trifluoride as such is not suitable for the production of $CF_3$—$CHCl_2$.

EXAMPLE 2

A) 340 g of an aluminium trifluoride essentially consisting of gamma-$AlF_3$ having a surface area of 28 $m^2/g$ was impregnated with a solution obtained by dissolving 52.3 g of $CrCl_3.6H_2$) in 58 ml of distilled water. The impregnation and the drying processes were the same as in Example 1. The dried catalyst was charged into the reactor of Example 1 and was heated up to 450° C. with air at a flow rate of 100 l/h. It was maintained at this temperature until only traces of chloride ions were present in the washing solution of the air leaving the reactor. Subsequently it was cooled with nitrogen. The Cr amount referred to the catalyst was of 3% by weight.

B) The catalyst of Example 2A (345 g) was charged into the apparatus of Example 1. At a reaction temperature of 360° C. and at a pressure slightly higher than the atmospheric pressure, 0.925 moles/h of $C_2Cl_4$ and 3.755 moles/h of HF were fed. In one hour there were collected 148 g of a reaction product, the molar composition of which was the following:

| | |
|---|---|
| $CF_3$—$CHClF$ | 9% |
| $CF_3$—$CHCl_2$ | 15.8% |
| $CCl_2$=$CClF$ + $CClF_2$—$CHCl_2$ | 5.7% |
| $C_2Cl_4$ | 64.0% |

The $C_2Cl_4$ conversion was of 36%. The $CF_3CHCl_2$ net yield was of 44%, the by-products net yield was of 25%.

EXAMPLE 3

Using the same catalyst of Example 2, the same apparatus of Example 1, a reaction temperature of 340° C. and a pressure slightly higher than the atmospheric pressure. 0.949 moles/h of $C_2Cl_4$ and 9.725 moles/h of HF were fed. Drawing was carried out for an hour, thereby collecting 153 g of a reaction product having the following molar composition:

| | |
|---|---|
| $CF_3$—$CHClF$ | 4.8% |
| $CF_3$—$CHCl_2$ | 14.8% |
| $CCl_2$=$CClF$ + $CClF_2$—$CHCl_2$ | 7.4% |
| $C_2Cl_4$ | 71.0% |

The $C_2Cl_4$ conversion was of 29%, the $ClF_3CHCl_2$ net yield was of 51% and the by-products net yield was of 16%.

EXAMPLE 4

A) 340 g of an aluminium trifluride containing 80% of gamma-$AlF_3$ having a surface area of 18 $m^2/g$ was impregnated a first time with a solution obtained by dissolving 52.3 g of $CrCl_3.6H_2O$ in 58 ml of distilled water. The impregnation and drying process was the same as in Example 1. After drying, the catalyst was impregnated a second time with the same amount of chromic solution having the same concentration, until a chrome content of 6% by weight was obtained.

The catalyst was then dried again, was charged into the reactor of Example 1 and was treated with a nitrogen flow (100 l/h) saturated with steam at 40°/50° C.

The treatment was carried out at 360° C. until only traces of chloride ions were present in the nitrogen washing solution leaving the reactor. Subsequently it was dried with dry nitrogen.

B) The catalyst of Example 4A (345 g) was placed into the paratus of Example 1. At a reaction temperature of 300° C., and at a pressure slightly higher than the atmospheric pressure there were fed 0.801 moles/h of $C_2Cl_4$ and 4.171 moles/h of HF. After a 1-hour drawing there were collected 130 g of a reaction product, the molar composition of which was as follows:

| | |
|---|---|
| $CF_3$—$CHClF$ | 2.2% |
| $CF_3$—$CHCl_2$ | 11.2% |
| $CCl_2$=$CClF$ + $CClF_2$—$CHCl_2$ | 8.1% |
| $C_2Cl_4$ | 76.7% |

The conversion of $C_2Cl_4$ was of 23.3%. The $CF_3CHCl_4$ net yield was of 48.1% and the net yield of by-products was of 9.4%.

EXAMPLE 5 (COMPARATIVE TEST)

A) To a solution of 10 kg of dodecahydrated chromic potassium alum [K Cr$(SO_4)_2$.12 $H_2O$] in 71.5 liters of water there was added, at room temperature and under stirring, an aqueous solution of ammonium hydroxide, containing about 10% by weight of $NH_3$, until the pH reached a value of 8.8. The hydrated chrome oxide suspension was further stirred for about 30 minutes at room temperature, taking care that the pH should remain between 8.8 and 9.0 by adding, if necessary, further amounts of $NH_4OH$.

The suspension was then diluted with deionized water till bringing the volume to about 160 liters, then it was allowed to decant for 24 hours, optionally accelerating decantation by means of a flocculating agent (for example it is possible to use from 30 to 40 ppm of ECOCLAR 2001 calculated on the slurry).

The highest possible amount of aqueous phase was then syphoned off and the operation was repeated (dilution with washing effect) further three times. After filtration, the hydrated chrome oxide cake was suspended in hot deionized water (85°–90° C.; 1,750 grams containing 15% of solid product suspended in three liters of water). Hot washing was repeated several times until the sulphate ions ($SO_4$−−) concentration was lower than 0.04% by weight referred to the calcined dry product. At last, the hydrated chrome oxide cake was suspended again in three liters of acetone at room temperature, thereby obtaining, by filtration, a hydrated chrome oxide, which was activated by calcination in a muffle furnace according to the following schedule:
5 hours at 100° C.
2 hours at 400° C.
from 4 to 5 hours at a temperature between 500° and 550° C.

Obtained were dark-green pellets having a content of $SO_4^{--}$ ions lower than 0.04% by weight and a specific surface area of about 88 m$^2$/g.

B) Into the apparatus of Example 1 there were charged 460 g of the catalyst of Example 5A in pellets, and, at a reaction temperature of 320° C. and at a pressure slightly higher than the atmospheric pressure, 1.163 moles/h of $C_2Cl_4$ and 4.341 moles/h of HF were fed. After a 1-hour drawing, 143 g of a reaction product having the following molar composition were recovered:

| | |
|---|---|
| $CF_3CHF_2$ | 10% |
| $CF_3CHClF$ | 6,1% |
| $CF_3CCl_2F$ | 4,6% |
| $CF_3CH_2Cl$ | 11,2% |
| $CF_3CCl_2H$ | 19,9% |
| $CCl_2=CClF + CClF_2-CHCl_2$ | 2% |
| $C_2Cl_4$ | 32,1% |

The $C_2Cl_4$ conversion was of 66.9%, the net yield of $CF_3-CHCl_2$ was of 29.7% and the non-recyclable by-products reached 67%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The references are hereby incorporated by reference.

What we claim is:

1. A continuous process for preparing 1,1,1-trifluoro-2,2-dichloroethane which comprises reacting perchloroethylene with HF in a gas phase in the presence of catalysts comprising $Cr_2O_3$ carried on $AlF_3$, without $Al_2O_3$, in the gamma and/or beta form, wherein reaction temperature ranges from 250° C. to 300° C.

2. A continuous process for preparing 1,1,1-trifluoro-2,2-dichloroethane which comprises reacting perchloroethylene with HF in a gas phase in the presence of catalysts comprising $Cr_2O_3$ carried on $AlF_3$, without $Al_2O_3$, in the gamma and/or beta form, wherein contact time between reagents and catalytic mass ranges from 3 seconds to 15 seconds.

3. A continuous process for preparing 1,1,1-trifluoro-2,2-dichloroethane which comprises reacting perchloroethylene with HF in a gas phase in the presence of catalysts comprising $Cr_2O_3$ carried on $AlF_3$, without $Al_2O_3$, in the gamma and/or beta form, wherein reaction temperature ranges from 250° C. to 300° C. and contact time between reagents and catalytic mass ranges from 3 seconds to 15 seconds.

* * * * *